(12) United States Patent
Smith et al.

(10) Patent No.: US 12,290,247 B2
(45) Date of Patent: May 6, 2025

(54) FEMALE URETHRAL CATHETERIZATION ASSIST DEVICE

(71) Applicants: Susan Smith, St. Marys, GA (US); Carl Hofstadter, Jr., Macon, GA (US)

(72) Inventors: Susan Smith, St. Marys, GA (US); Carl Hofstadter, Jr., Macon, GA (US)

( * ) Notice: Subject to any disclaimer, the term of this patent is extended or adjusted under 35 U.S.C. 154(b) by 290 days.

(21) Appl. No.: 18/158,498

(22) Filed: Jan. 24, 2023

(65) Prior Publication Data

US 2023/0157532 A1 May 25, 2023

Related U.S. Application Data

(63) Continuation-in-part of application No. 15/782,237, filed on Oct. 12, 2017, now Pat. No. 11,583,660.

(60) Provisional application No. 62/407,039, filed on Oct. 12, 2016.

(51) Int. Cl.
*A61B 1/32* (2006.01)
*A61B 1/303* (2006.01)
*A61M 25/00* (2006.01)
*A61M 25/01* (2006.01)

(52) U.S. Cl.
CPC ............... *A61B 1/32* (2013.01); *A61B 1/303* (2013.01); *A61M 25/0017* (2013.01); *A61M 25/01* (2013.01)

(58) Field of Classification Search
CPC .......... A61M 25/01; A61M 2210/1092; A61M 25/0111; A61B 17/0206; A61B 17/44; A61B 17/2812; A61B 17/4241; A61B 18/085; A61B 18/1445; A61B 2018/00601; A61B 17/32; A61B 17/29; A61B 17/320016; A61B 34/70; A61B 2017/2837; A61B 17/42; A61B 17/28; A61F 5/455

See application file for complete search history.

(56) References Cited

U.S. PATENT DOCUMENTS

| | | |
|---|---|---|
| 2,583,892 A | 1/1952 | Michael |
| 4,023,560 A * | 5/1977 | Cade ............... A61F 5/455 600/574 |
| 4,502,485 A | 3/1985 | Burgin |
| 4,559,944 A | 12/1985 | Jaeger |
| 5,569,300 A | 10/1996 | Redmon |
| 5,626,606 A * | 5/1997 | Schellpfeffer ..... A61B 17/2812 606/205 |
| 5,849,017 A | 12/1998 | Reynolds et al. |
| 6,302,842 B1 | 10/2001 | Auerbach et al. |
| 7,083,613 B2 | 8/2006 | Treat |
| 7,104,980 B1 | 9/2006 | Laherty et al. |
| 2003/0055319 A1 | 3/2003 | Chang |
| 2005/0027170 A1 | 2/2005 | Nohara et al. |
| 2005/0267336 A1 | 12/2005 | Bertolero et al. |

(Continued)

*Primary Examiner* — Kai H Weng
*Assistant Examiner* — Alessandro R Del Priore
(74) *Attorney, Agent, or Firm* — Boudwin Intellectual Property Law, LLC; Daniel Boudwin

(57) ABSTRACT

A female urethral catheterization assist device is provided. The female urethral catheterization assist device includes a first lateral arm pivotally secured to a second lateral arm. Each lateral arm includes a platform placed opposite a handle. A paddle extends upward from each platform on an interior lateral side of each platform. The paddles are designed to engage the labia minora and labia majora of a patient and to assist with urethral catheterization.

7 Claims, 4 Drawing Sheets

(56) References Cited

U.S. PATENT DOCUMENTS

| | | |
|---|---|---|
| 2006/0100607 A1 | 5/2006 | Brown |
| 2010/0317928 A1 | 12/2010 | Subramaniam |
| 2012/0296172 A1 | 11/2012 | Raven, III et al. |
| 2017/0311942 A1 | 11/2017 | Daavettila et al. |

* cited by examiner

FEMALE URETHRAL CATHETERIZATION ASSIST DEVICE

CROSS REFERENCE TO RELATED APPLICATIONS

This application claims the benefit of U.S. Non-Provisional application Ser. No. 15/782,237 filed on Oct. 12, 2017, which claims the benefit of U.S. Provisional Application No. 62/407,039 filed on Oct. 12, 2016. The above identified patent application is herein incorporated by reference in its entirety to provide continuity of disclosure.

BACKGROUND OF THE INVENTION

The present invention relates to The present invention relates to a device and method of inserting a female urethral catheter. More specifically, the present invention provides a female urethral catheterization assisting device having a pair of opposing lateral arms pivotally connected so as to allow for the selective opening and closing thereof. The lateral arms each include a paddle disposed at a distal end that extends from a first side that engages with a labia minora and majora of a female patient and exposes the urinary meatus.

Currently, when a female patient undergoes catheterization, a medical worker must use a short, small device to retract the labia minora and labia majora to expose the urinary meatus. Because this requires the medical worker to place her or his hands in the vicinity of a sensitive area of the patient, this can be an unpleasant and uncomfortable experience for both the patient and the medical worker. Additionally, these known devices fail to provide a female urethral catheterization assisting device that provides a full and clear view of the urethral opening for ease of catheterization by clinical or non-clinical persons.

In light of the devices disclosed in the known art, it is submitted that the present invention substantially diverges in design elements from the devices in the known art and consequently it is clear that there is a need in the art for an improvement to existing female urethral catheter devices. In this regard, the instant invention substantially fulfills these needs.

SUMMARY OF THE INVENTION

In view of the foregoing disadvantages inherent in the known types of female catheterization devices now present in the prior art, the present invention provides a female urethral catheterization assist device wherein the same can be utilized for providing convenience for the user when performing catheterization upon a female patient.

The female urethral catheterization assist device comprises a pair of lateral arms comprising a first lateral arm and a second lateral arm. The first lateral arm has a first handle at a proximal end. The second lateral arm has a second handle at a proximal end. The first handle and the second handle are designed to be engaged by a user's fingers. The first lateral arm is secured to the second lateral arm by a pivot. The pivot is disposed intermediately between the proximal ends and distal ends of the first lateral arm and the second lateral arm and enables bilateral and unrestricted rotation of the first lateral arm and the second lateral arm. The distal end of the first lateral arm comprises a first platform and the distal end of the second lateral arm comprises a second platform. The first platform and the second platform each comprise a pair of curved lateral sides. The pair of curved lateral sides consist of an interior lateral side and an exterior lateral side. The first platform and the second platform are each dimensioned to receive a finger thereon. The first platform comprises a first paddle disposed on the interior lateral side of the first platform of the first lateral arm, forming a flush surface therewith. The second platform comprises a second paddle disposed on the interior lateral side of the second platform of the second lateral arm, forming a flush surface therewith. Each paddle defines a base in contact with the interior lateral side of the lateral arm. Each paddle is of an arcuate profile and comprising a singular apex extending inwardly from the lateral arm. Each paddle extends linearly upward entirely from the base of each paddle to a top edge thereof. The singular apex of the first lateral arm and the singular apex of the second lateral arm contact each other in the closed configuration.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
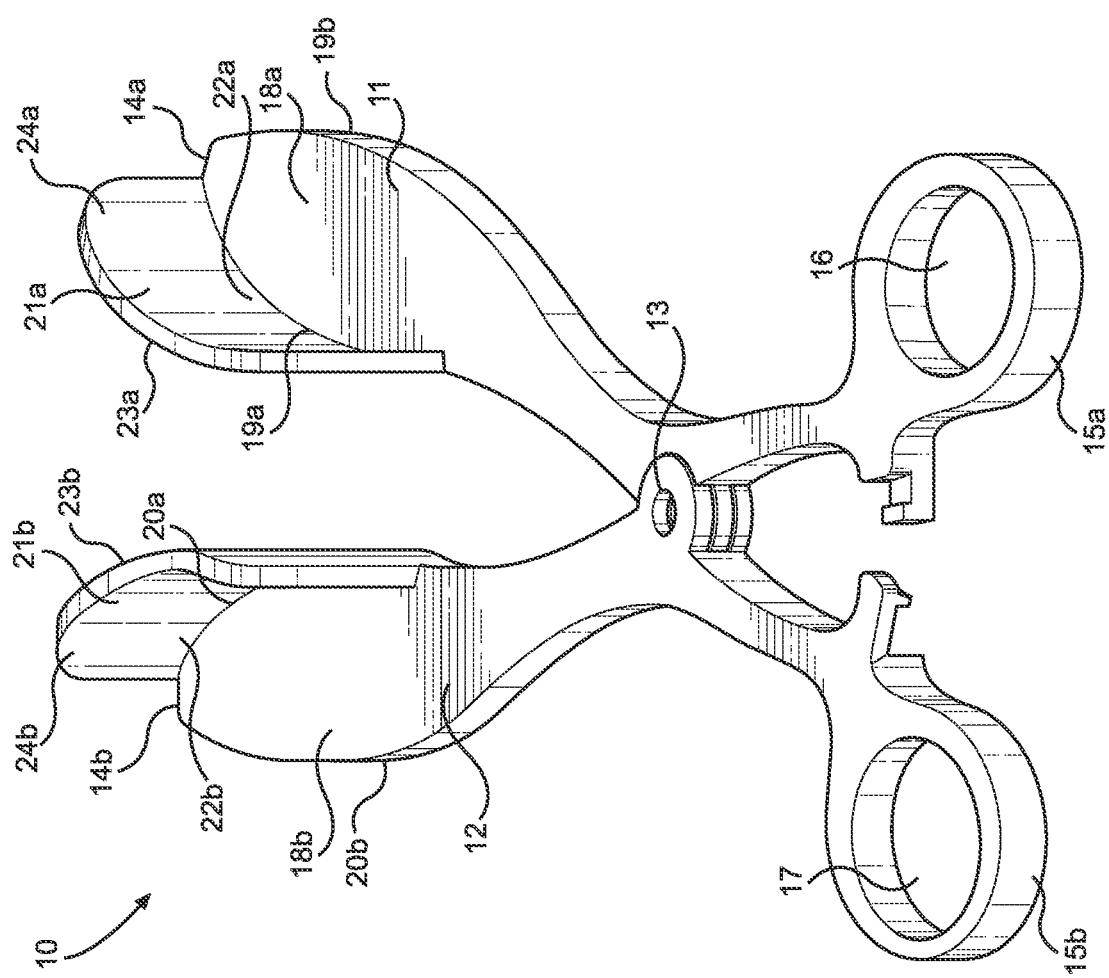
FIG. 1 shows a perspective view of the female urethral catheter assist device.

Reference is made herein to the attached drawings. Like reference numerals are used throughout the drawings to depict like or similar elements of the XXX. The figures are intended for representative purposes only and should not be considered to be limiting in any respect.

Figure 2:
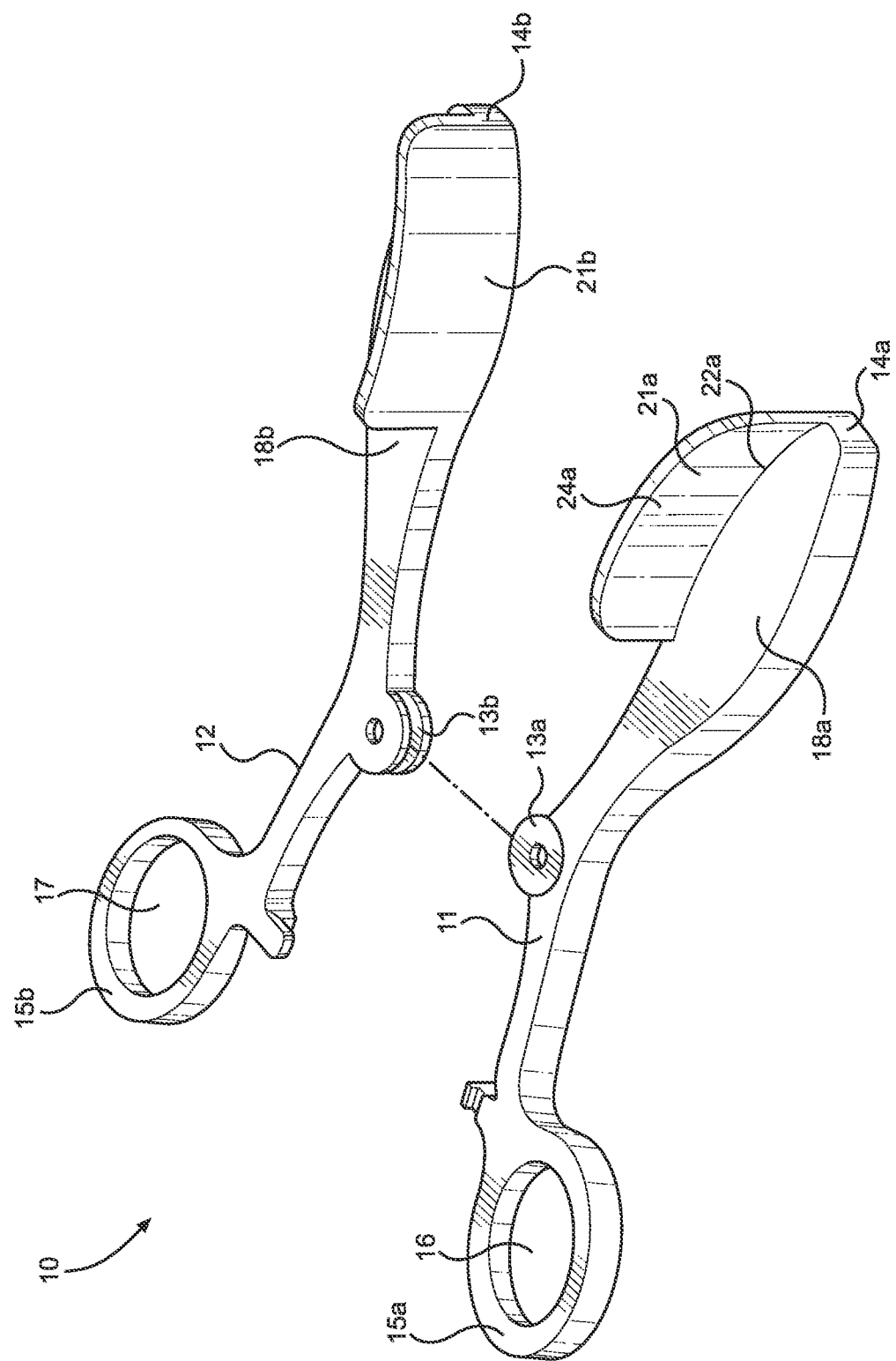
FIG. 2 shows an exploded view of an embodiment of the female urethral catheter assist device.

Referring now to FIGS. 1 and 2, there is shown a perspective view and an exploded view of an embodiment of the female urethral catheter assist device, respectively. The female urethral catheter assist device 10 provides a medical device that is configured to engage with a labia minora and majora to expose the urinary meatus of a patient, and therefore allow for the insertion of a female urethral catheter therein.

The female urethral catheter assist device 10 comprises a pair of lateral arms 11, 12. In the illustrated embodiment, the pair of lateral arms 11, 12 consists of a first lateral arm 11 and a second lateral arm 12. Each lateral arm 11, 12 defines a proximal end 14a, 14b disposed opposite a distal end 15a, 15b. In the illustrated embodiment, each lateral arm 11, 12 is integrally formed, such the components defined thereby are substantially rigid, secured, and inseparable.

The first lateral arm 11 and the second lateral arm 12 are connected at a pivot 13 that interconnects a portion of the first lateral arm 11 with a portion of the second lateral arm 12. The pivot 13 is disposed intermediate to the proximal end 14a, 14b and a distal end 15a, 15b of the first lateral arm 11 and the second lateral arm 12. The pivot 13 is configured to enable bilateral and unrestricted rotation of the first lateral arm 11 and the second lateral arm 12.

The first lateral arm 11 comprises a first handle 16 disposed at the proximal end 15a of the first lateral arm 11. The first handle 16 is configured to be engaged by a first finger of the user. The second later arm 12 comprises a second handle 17 disposed at the proximal end 15b of the second lateral arm 12. The second handle 12 is configured to be engaged by a fourth finger of the user.

The distal end 14a of the first lateral arm 11 comprises a first platform 18a. The first platform 18a comprises a pair of curved lateral sides 19a, 19b. The pair of curved lateral sides 19a, 19b consists of an interior lateral side 19a and an exterior lateral side 19b. The interior lateral side 19a curves outwardly from the first platform 18a towards the second platform 18b. The exterior lateral side 19b curves outwardly from the first platform 18a, away from the second platform 18b. As such, an oval-shaped area is defined by the first platform 18a. The first platform 18a is dimensioned to receive a finger thereon.

The distal end 14b of the second lateral arm 12 comprises a second platform 18b. The second platform 18a comprises a pair of curved lateral sides 20a, 20b. The pair of curved lateral sides 20a, 20b consists of an interior lateral side 20a and an exterior lateral side 20b. The interior lateral side 20a curves inwardly from the second platform 18b towards the first platform 18a. The exterior lateral side 20b curves outwardly from the second platform 18b away from the first platform 18a. As such, an oval-shaped area is defined by the second platform 18b. The second platform 18b is dimensioned to receive a finger thereon.

A first paddle 21a is disposed on the interior lateral side 19a of the first platform 18a of the first lateral arm 11. The first paddle 21a forms a flush surface with the interior lateral side 19a of the first lateral arm 11. The first paddle 21a defines a base 22a in contact with the interior lateral side 19a of the first lateral arm 11. The first paddle 21a is of an arcuate profile, defining a singular apex 23a, and extends inwardly from the first arcuate arm 11, along the perimeter of the interior lateral side 19a. The first paddle 21a extends linearly upward from the base 22a to a top end 24a of the first paddle 21a. The first paddle 21a comprises a flat surface disposed at the top end 24a thereof, such as to prevent the first paddle 21a from cutting the skin.

Figure 3A:
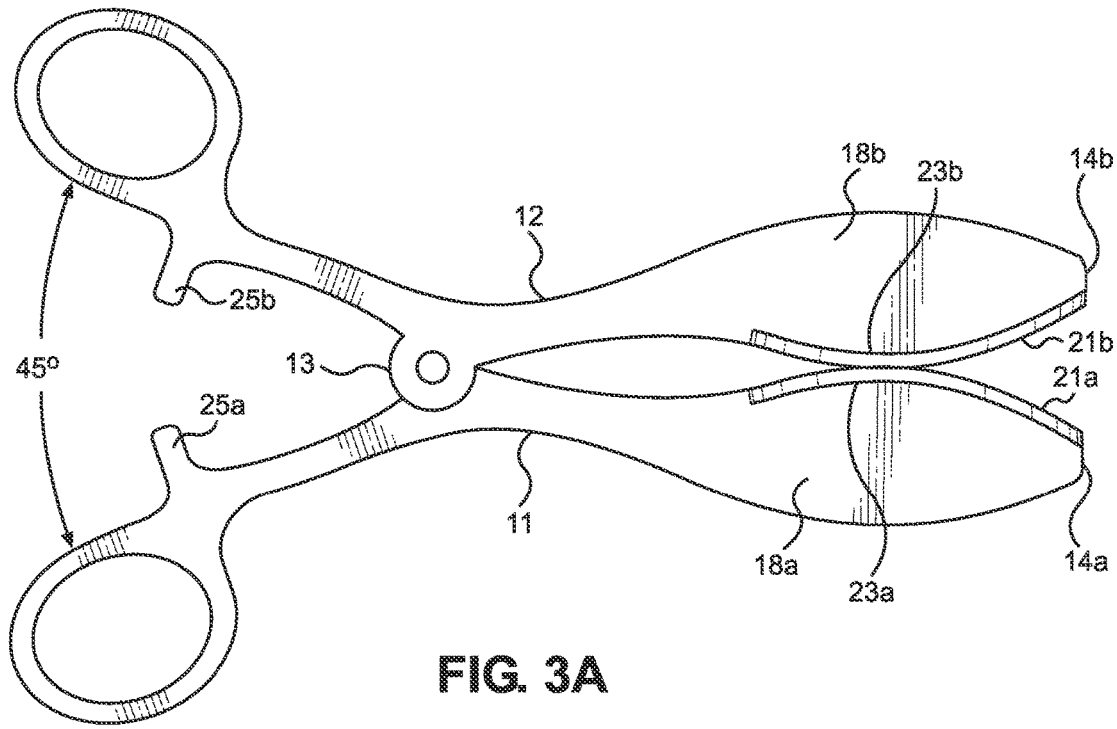
FIG. 3A shows an overhead view of an embodiment of the female urethral catheter assist device in a closed configuration.
Figure 3B:
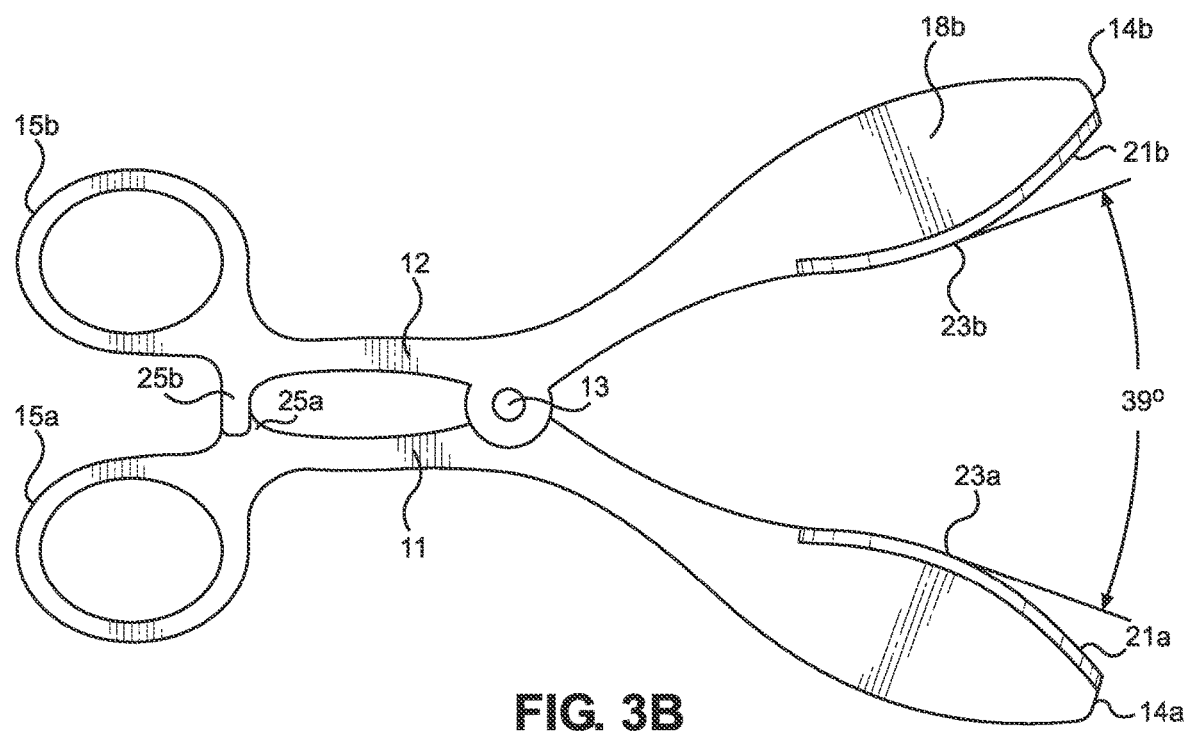
FIG. 3B shows an overhead view of an embodiment of the female urethral catheter assist device in an open configuration.

A second paddle 21b is disposed on the interior lateral side 20a of the second platform 18b of the second lateral arm 12. The second paddle 21b forms a flush surface with the interior lateral side 20b of the second lateral arm 12. The second paddle 21b defines a base 22b in contact with the interior lateral side 20a of the second lateral arm 12. The second paddle 21b is of an arcuate profile, defining a singular apex 23b, and extends inwardly from the second arcuate arm 12, along the perimeter of the interior lateral side 20a. The second paddle 21b extends linearly upward from the base 22b to a top end 24b of the second paddle 21b. The second paddle 21b Referring now to FIGS. 3A and 3B, there is shown an overhead view of an embodiment of the female urethral catheter assist device in the closed configuration and an overhead view of an embodiment of the female urethral catheter assist device in the open configuration, respectively. As demonstrated, the female urethral catheter assist device 10 is movable about the pivot 13 between a closed configuration (shown in FIG. 3A) and an open configuration (shown in FIG. 3B). The female urethral catheter assist device 10 is usable in any number of intermediate positions defined between the open configuration and the closed configuration. Furthermore, the female urethral catheter assist device 10 is freely movable in both directions around the pivot 13, such as to prevent excessive pressure from being applied to the patient.

The closed configuration (shown in FIG. 3A) is defined where the singular apex 23a of the first paddle 21a of the first lateral arm 11 contacts the singular apex 23b of the second paddle 21b of the second lateral arm 12. When in the closed configuration, or in a configuration closer to the closed configuration relative to the open configuration, the first paddle 21a and the second paddle 21b may be more easily positioned into a narrow space, such as the space between the labial minora and majora of a patient undergoing catheterization.

The open configuration (shown in FIG. 3B) is defined where a fastener 25a, 25b is engaged. The fastener 25a, 25b comprises a first member 25a and a second member 25b, wherein the first member 25a is configured to engage and couple with the second member 25b, restricting movement of the first lateral arm 11 and the second lateral arm 12. The first member 25a is disposed on an interior side of the first lateral arm 11, facing the second lateral arm 12, between the pivot 13 and the proximal end 15a of the first lateral arm 11. The second member 25b is disposed on an interior side of the second lateral arm 12, facing the first lateral arm 11, between the pivot 13 and the proximal end 15b of the second lateral arm 12. In the illustrated embodiment, the fastener 25a, 25b comprises a first member 25a comprising a transverse bar and a second member 25b comprising a latch.

Figure 4:
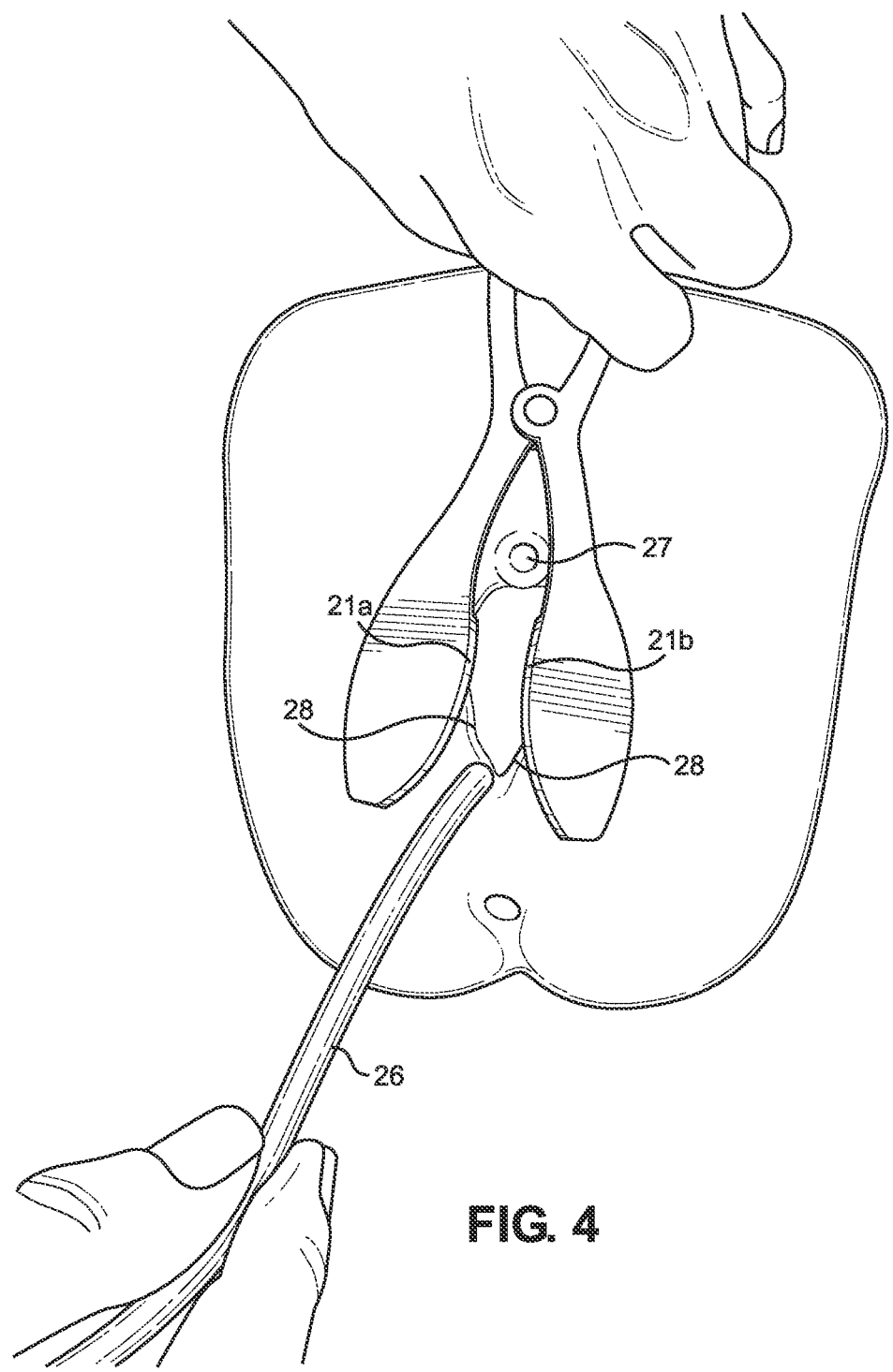
FIG. 4 shows an in-use view of an embodiment of the female urethral catheter assist device.

Referring now to FIG. 4, there is shown an in-use view of an embodiment of the female urethral catheter assist device. In use, a female urethral catheter 26 may be inserted into a urethra 27 with assistance from the female urethral catheterization assist device. The paddles 21a, 21b of the female urethral catheterization assist device may be utilized to gently engage with a labia minora and/or labia majora 28 of the patient. Once engaged, the female urethral catheterization assist device to a relatively open configuration to expose the urethra 27. The female urethral catheter 26 may then be inserted into the urethra 27 completing the catheterization.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A female urethral catheterization assist device, comprising:
   a pair of lateral arms comprising a first lateral arm and a second lateral arm;
   the first lateral arm having a first handle at a proximal end;

the second lateral arm having a second handle at a proximal end;
wherein the first handle is configured to be engaged by a finger of the user;
wherein the second handle is configured to be engaged by a finger of the user;
a pivot interconnecting the first lateral arm and the second lateral arm;
the pivot disposed intermediate the proximal end and a distal end of the first lateral arm and the second lateral arm;
the pivot configured to enable bilateral and unrestricted rotation of the first lateral arm and the second lateral arm;
the distal end of the first lateral arm comprising a first platform;
the distal end of the second lateral arm comprising a second platform;
the first platform and the second platform each comprising a pair of curved lateral sides,
wherein the pair of curved lateral sides consists of an interior lateral side and an exterior lateral side;
wherein the first platform is dimensioned to receive a finger of the user;
wherein the second platform is dimensioned to receive a finger of the user;
the exterior lateral side curving outwardly from each platform, away from the opposing platform;
the interior lateral side curving outwardly from each platform, towards the opposing platform;
a first paddle disposed on the interior lateral side of the first platform of the first lateral arm, forming a flush surface therewith;
a second paddle disposed on the interior lateral side of the second platform of the second lateral arm, forming a flush surface therewith;
each paddle defining a base in contact with the interior lateral side of the lateral arm;
each paddle being of an arcuate profile and comprising a singular apex extending inwardly from the lateral arm;
each paddle extending linearly upward entirely from the base of each paddle to a top edge thereof;
wherein the singular apex of the first lateral arm and the singular apex of the second lateral arm contact each other in the closed configuration.

2. The female urethral catheterization assist device of claim 1, further comprising a fastener disposed on a side of an arm of the pair of arms most adjacent to the opposing arm, the fastener configured to selectively couple the proximal end of the first lateral arm to the proximal end of the second lateral arm, inhibiting movement of the first lateral arm and the second lateral arm in any direction and forming a locked configuration.

3. The female urethral catheterization assist device of claim 2, wherein the fastener comprises a transverse bar with a latch configured to couple with a mating fastener disposed on the opposing lateral arm.

4. The female urethral catheterization assist device of claim 1, wherein each lateral arm is integrally formed.

5. The female urethral catheterization assist device of claim 1, wherein the proximal end of the first lateral arm and the second lateral arm contact each other in the open configuration.

6. The female urethral catheterization assist device of claim 1, wherein the paddles are configured to not cut.

7. The female urethral catheterization assist device of claim 1, wherein the first handle comprises a first aperture adapted to receive a first finger therethrough and the second handle comprises a second aperture adapted to receive a fourth finger therethrough.

* * * * *